US005902298A

United States Patent [19]

Niedospial, Jr. et al.

[11] Patent Number: 5,902,298

[45] Date of Patent: May 11, 1999

[54] MEDICAMENT CONTAINER STOPPER WITH INTEGRAL SPIKE ACCESS MEANS

[75] Inventors: John J. Niedospial, Jr., Burlington, N.J.; Mark E. Gabbard, Salisbury, Md.

[73] Assignee: Bracco Research USA, Princeton, N.J.

[21] Appl. No.: 08/966,433

[22] Filed: Nov. 7, 1997

[51] Int. Cl.$^{6}$ ............................ A61B 19/00; B65D 41/20

[52] U.S. Cl. ............................ 604/414; 604/411; 215/247

[58] Field of Search .................................... 604/403, 404, 604/407, 411, 412, 414, 415, 416, 905; 215/247, 249, 250, 47, 48, 50

[56] References Cited

U.S. PATENT DOCUMENTS

| | | | |
|---|---|---|---|
| 2,289,677 | 7/1942 | Perelson | 215/47 |
| 2,326,490 | 8/1943 | Perelson | 215/47 |
| 2,342,215 | 2/1944 | Perelson | 215/38 |
| 2,667,986 | 2/1954 | Perelson | 215/48 |
| 3,872,992 | 3/1975 | Larson | 215/249 |
| 3,940,003 | 2/1976 | Larson | 215/247 |
| 3,977,555 | 8/1976 | Larson | 215/247 |
| 4,412,623 | 11/1983 | Schmidt | 215/11 |
| 5,232,109 | 8/1993 | Tirrell et al. | 215/247 |
| 5,364,386 | 11/1994 | Fukuoka et al. | 215/411 |
| 5,429,256 | 7/1995 | Kestenbaum | 215/247 |
| 5,433,330 | 7/1995 | Yatsko et al. | 215/247 |
| 5,487,737 | 1/1996 | Meyer | 604/403 |
| 5,580,351 | 12/1996 | Helgren et al. | 604/411 |
| 5,620,434 | 4/1997 | Brony | 604/406 |
| 5,772,652 | 6/1998 | Zielinski | 604/411 |
| 5,785,701 | 7/1998 | Sams et al. | 604/411 |
| 5,817,082 | 10/1998 | Niedospial, Jr. et al. | 604/414 |

*Primary Examiner*—John G. Weiss
*Assistant Examiner*—David J. Cho
*Attorney, Agent, or Firm*—Imre Balogh

[57] ABSTRACT

A closure assembly/container combination for delivering media fluid to a patient by needleless access means. The closure assembly comprises an elastomeric stopper for sealing the container at its open end and a spike access means equipped with a luer connector.

20 Claims, 5 Drawing Sheets

MEDICAMENT CONTAINER STOPPER WITH INTEGRAL SPIKE ACCESS MEANS

BACKGROUND OF THE INVENTION

1. Field of the Invention

This invention relates to a stopper having a spike access means used in conjunction with containers such as bottles, vials and bags containing pharmaceutical products for parenteral administration. More particularly, the invention relates to an elastomeric stopper for hermetically sealing a parenteral container, bottle, vial or bag the contents of which is accessed by the use of a spike integral with the stopper.

2. Reported Developments

The prior art has developed numerous devices to prevent accidental needle strike injuries to practitioners and patients. Such injuries are known to spread infectious diseases including hepatitis and AIDS. One of the main features of these devices is the lack of exposed sharp needles. The closures or stoppers have built in access means to the content of the containers, such as vials, cartridges, bags and bottles. The closures or stoppers in these devices serve the dual function of hermetically sealing the container while allowing access to the content therethrough.

Stopper systems for containers such as vials and bottles are made of materials that are resistant to chemicals and pharmaceuticals such as corrosive materials, reagents, parenteral solutions and solid formulations reconstitutable with a solvent prior to use. The most commonly used stopper/container system for such products has been glass or plastic bottles and vials equipped with rubber stoppers made of elastomeric materials. The system provides for good hermetical seal, safe storage and easy access to the content through the elastomeric stopper via the use of an infusion spike or a syringe when withdrawal of the content is desired. The elastomeric stopper used generally comprises an elastomeric base, such as natural or synthetic rubber and an inert coating covering at least some portions of the stopper. The coating used includes chlorobutyl rubber, polymeric fluorocarbon resins such as polytetrafluoroethylene and various thermoplastic films. The coating is intended to insulate the elastomeric stopper base from the contents of the container in order to prevent contact and possible chemical reactions therebetween.

Generally, the elastomeric stopper is of cylindrical shape and has a flange head portion overlying the open top end of the container. Integral with the head portion is a body portion which extends into the open end and seated in the neck portion of the container, the diameter of the body portion being somewhat larger than the inside diameter of the container so that a tight seal is created between the body portion and the wall of the container. The lower end of the body portion is beveled towards the central, longitudinal axis of the body portion to facilitate the insertion of the body portion into the container. The circular bottom surface that faces the contents of the container is substantially planar and is imperforate, having no recess therein. The head portion of the stopper is provided with a central recess extending downwardly from the top thereof a substantial distance into the body portion so that the central recess and the circular bottom surface define a diaphragm. The walls forming the recess are generally cylindrical but may be provided with one or more circular protuberances extending inwardly to terminate just short of the center line of the stopper. The circular protuberances serve to press against and hold the needle of a syringe when the needle is inserted through the recess to penetrate the diaphragm for removal of the contents of the container. The elastomeric stopper is held in position by a metal ring or cap usually constructed of aluminum. The metal ring or cap has a removable center opening for allowing insertion of the syringe needle into the container.

Another type of the prior art stoppers has the needle penetrable diaphragm on the top portion of the stopper.

Various stopper and access systems exist in the prior art to hold and remove the contents of containers which are illustrated hereunder.

U.S. Pat. Nos. 2,289,677 and 2,326,490 disclose a rubber stopper for use in vials comprising: an outer wall which serves as a seal between the vial and the stopper; and an inner wall forming a chamber in the center of the stopper, the bottom portion of the inner wall serving as a diaphragm. A hollow needle, having a sharp end for piercing the diaphragm, and an outer end exposed for connection with a syringe, is carried by the outer wall. A syringe connected to the outer end of the needle and pushed inwardly effects piercing of the diaphragm thereby permitting aspiration of the contents of the vial.

U.S. Pat. No. 2,342,215 discloses a dispensing and sealing stopper for a vial comprising: a stopper body having a hollow needle therein, one end of said hollow needle is in constant communication with the contents of the vial, and the other end is sealed by a penetrable, thin membrane. When withdrawal of the contents of the vial is desired, a syringe is inserted into the stopper to penetrate the thin membrane and to engage the other end of the hollow needle. When the syringe is removed, the thin membrane self-closes to maintain the hollow needle and the contents of the vial sterile.

U.S. Pat. No. 5,232,109 discloses an elastomeric stopper for a bottle, said stopper includes an annular protuberance which forms a second seal with the shaft of a spike inserted in the stopper to prevent leakage, blow-out and introduction of particulate matter into the fluid-containing bottle.

U.S. Pat. No. 5,364,386 relates to an infusion unit which comprises: a flexible, large container, a small medicine vial and a pipe which serves to communicate between the large, flexible container and the small medicine vial.

The large container is adapted to hold a solvent or diluent, while the medicine vial contains a powdery medicine which is to be mixed and dissolved in the solvent or diluent contained in the large, flexible container. Upon dissolution, the mixed medicine is discharged through an outlet at the lower end of the large container for infusion into a patient.

U.S. Pat. No. 5,429,256 pertains to a drug withdrawal system for a vial. The withdrawal system comprises: a vial containing a medicament therein and closed with a rubber gasket; and an apparatus which snap fits on top of the vial. The apparatus comprises: a chassis and a cap which is attached to the cap by a living hinge.

The chassis is cylindrical and has vertical grooves on the external sides to facilitate handling. The top of the chassis has a central opening. The chassis includes a male luer lock adapter having external threads thereon, and a ferrule structure the lower end of which has a hollow sharpened lance. The apparatus is used with a syringe having a female luer lock connector which snap fits with the male luer lock adapter.

In use, the cap cover is opened, and a syringe is screwed onto the outer end of the adapter. The syringe is then tightened on the adapter which moves the lance downward and the lance penetrates the gasket on the vial thereby establishing flow communication with the content of the vial. The content of the vial is withdrawn by pulling back on the plunger of the syringe. The syringe is then removed with the content therein ready to receive a needle assembly for injecting the content into a patient.

U.S. Pat. No. 5,433,330 relates to a needleless access stopper used on containers with a cannula having a blunt stopper penetrating tip.

The present invention provides sealing and needleless access means for containers, such as bottles or vials made of glass or plastic, and bottles and bags made of plastic containing medical fluids, such as x-ray contrast media and parenteral liquids. The needleless access means provides for hermatic sealing, safe handling, sterilization and storing. For convenience the invention will be described in combination with glass medicinal bottles. It is to be understood, however, that the invention includes sealing and access means for containers in general which comprise rigid or semi rigid access ports and are capable of receiving such sealing and access means.

SUMMARY OF THE INVENTION

In accordance with the present invention, a closure assembly/container combination is provided wherein said container contains a medical fluid therein, and said closure having a needleless access means allowing withdrawal of the medical fluid from the container by the use of an intravenous tubing, a syringe or a mating luer connector attached to the needleless access means, said closure/container combination comprising:

a) a container containing a medical fluid therein and having a neck portion terminating in an open end;

b) a closure assembly comprising:

1) an elastomeric stopper hermetically seating the container at its open end;

2) a cylindrical collar fastened over portions of the elastomeric stopper and the container to hold the elastomeric stopper in the container, said cylindrical collar having a central opening in its flat top portion to allow access to a spike access means located in the elastomeric stopper;

3) a spike access means located in the upper center portion of the elastomeric stopper comprising:

i) a spike housing defined by a cylindrical side wall, a horizontal stopper membrane forming the bottom of the spike housing, and a removable sterility seal on the top portion of the spike housing;

ii) a spike having a male luer element and located in the spike housing;

iii) a male luer connector on the exterior of the spike housing; said male luer connector and male luer element are designed to twistably engage a female luer coupling to force the spike towards and penetrate the horizontal stopper membrane and thereby establish fluid communication with the contnet of the container; and iv) a cap covering the cylindrical collar over the container.

It is understood that the container referred to includes bottles, vials and bags of various configurations, such as round, rectangular and oval. The neck portion of the container, however, should be sufficiently rigid in order to accommodate the closure assembly therein.

BRIEF DESCRIPTION OF THE DRAWINGS

With reference to the annexed drawings, illustrating the invention.

DESCRIPTION OF THE PREFERRED EMBODIMENT

Figure 1B:
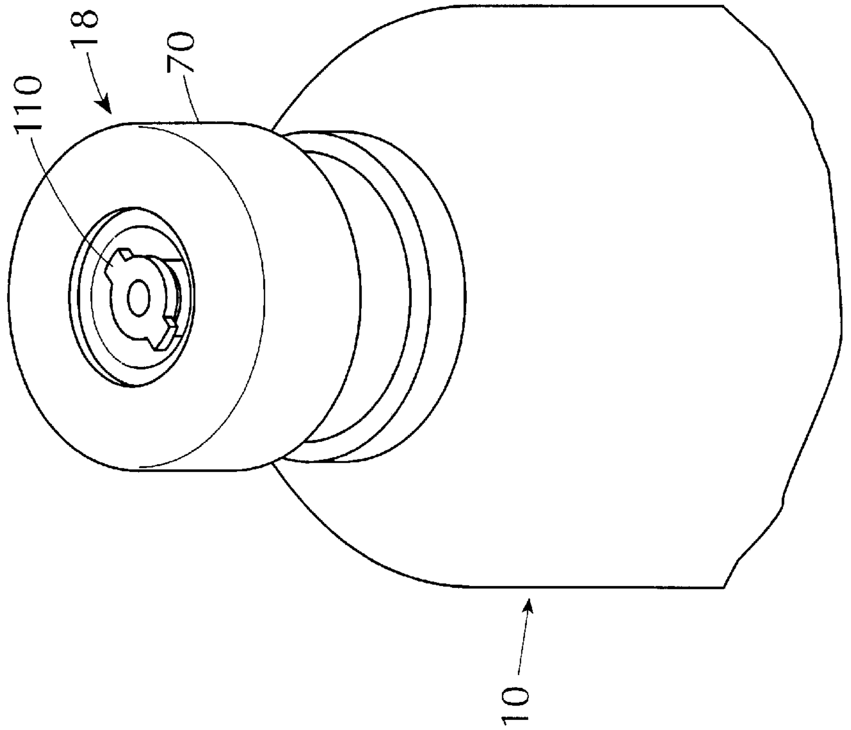
FIG. 1B is a perspective view of the container, the stopper with spike access means shown in FIG. 1A without the cap.
Figure 1A:
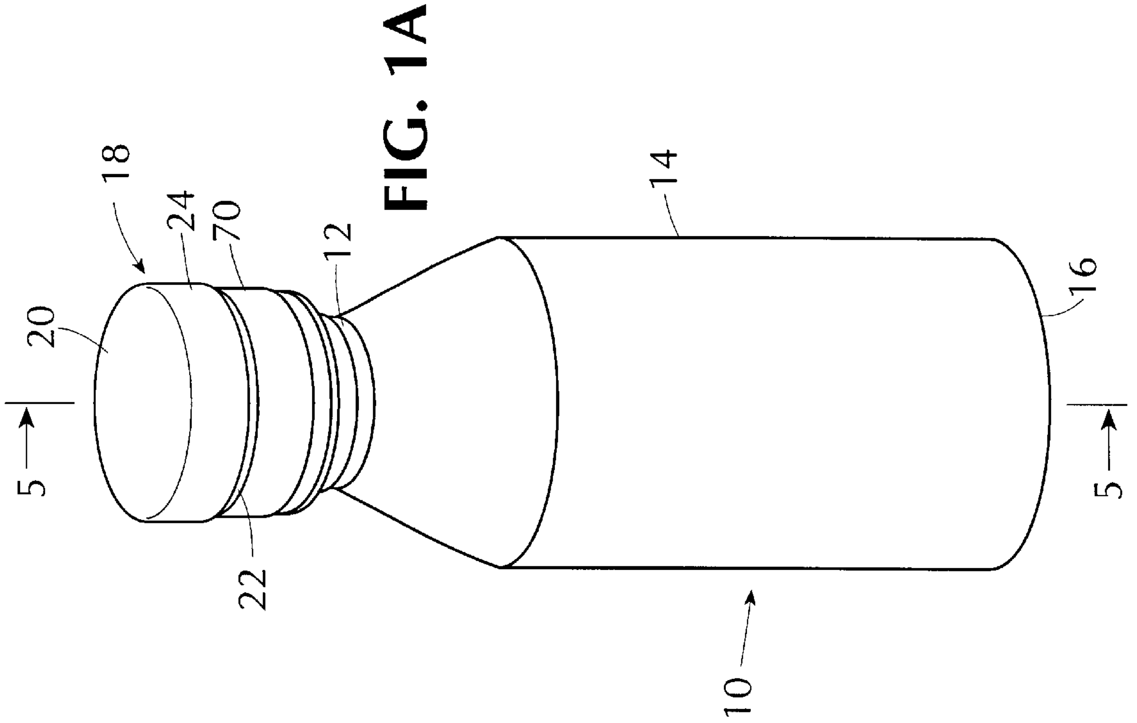
FIG. 1A is a perspective view of a container, a stopper with spike access means, and a cap.
Figure 2:
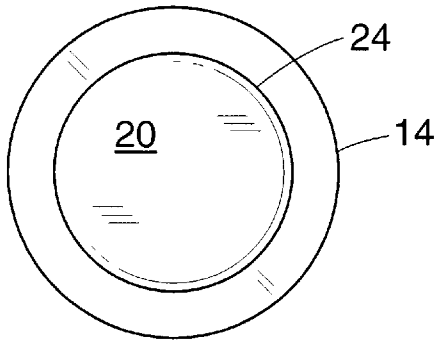
FIG. 2 is a top plan view of the container, the stopper with spike access means, and the cap shown in FIG. 1A.
Figure 4:
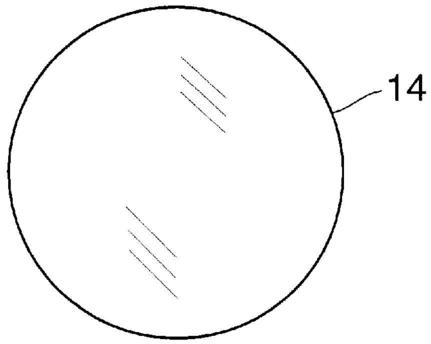
FIG. 4 is a bottom plan view of the container, stopper with spike access means, and the cap shown in FIG. 1A.
Figure 3:
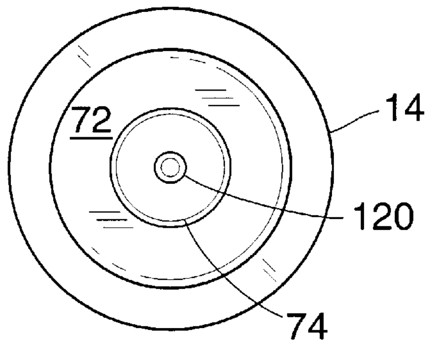
FIG. 3 is a top plan view of the container, the stopper with spike access means shown in FIG. 1B.
Figure 7:
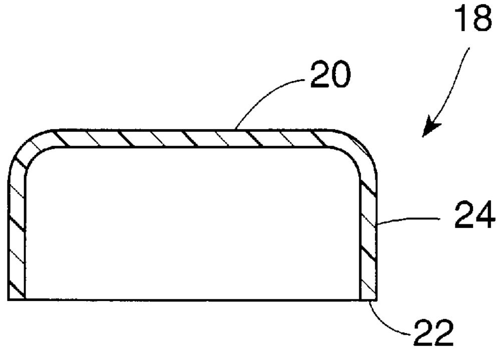
FIG. 7 is a sectional view of the cap removed form the container shown in FIG. 1A.

Referring to FIGS. 1A, 1B, 5 and 6, the container 10 having an open end in which the closure assembly of the present invention is used comprises a neck portion 12, a side portion 14, and a bottom portion 16. The closure assembly is covered with a cylindrical removable cap 18 having a flat top portion 20, a bottom portion 22 which is removably attached to the top cylindrical collar portion 70 of the container 10.

Figure 5:
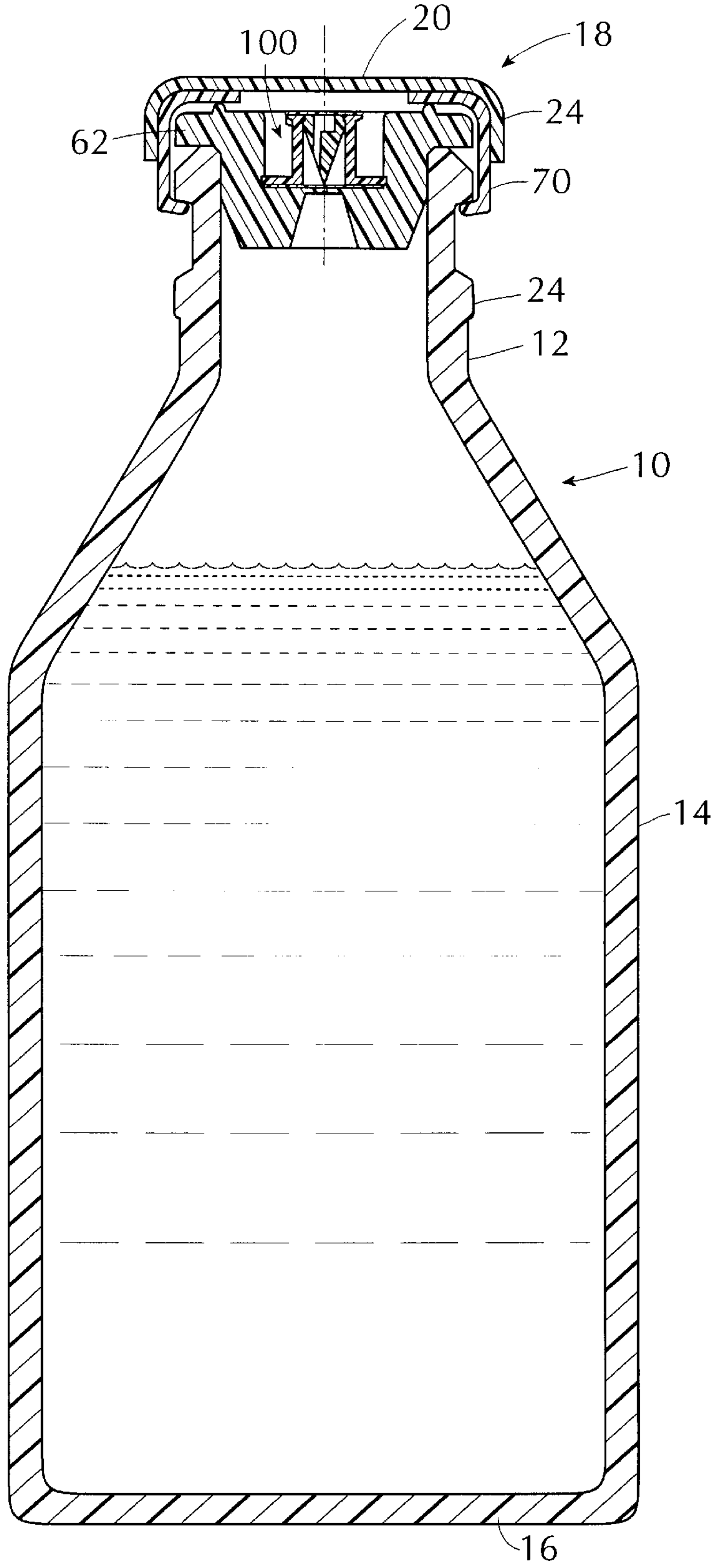
FIG. 5 is a sectional view of the container, the stopper with the spike access means and the cap taken along the line 5—5 of FIG. 1A.
Figure 6:
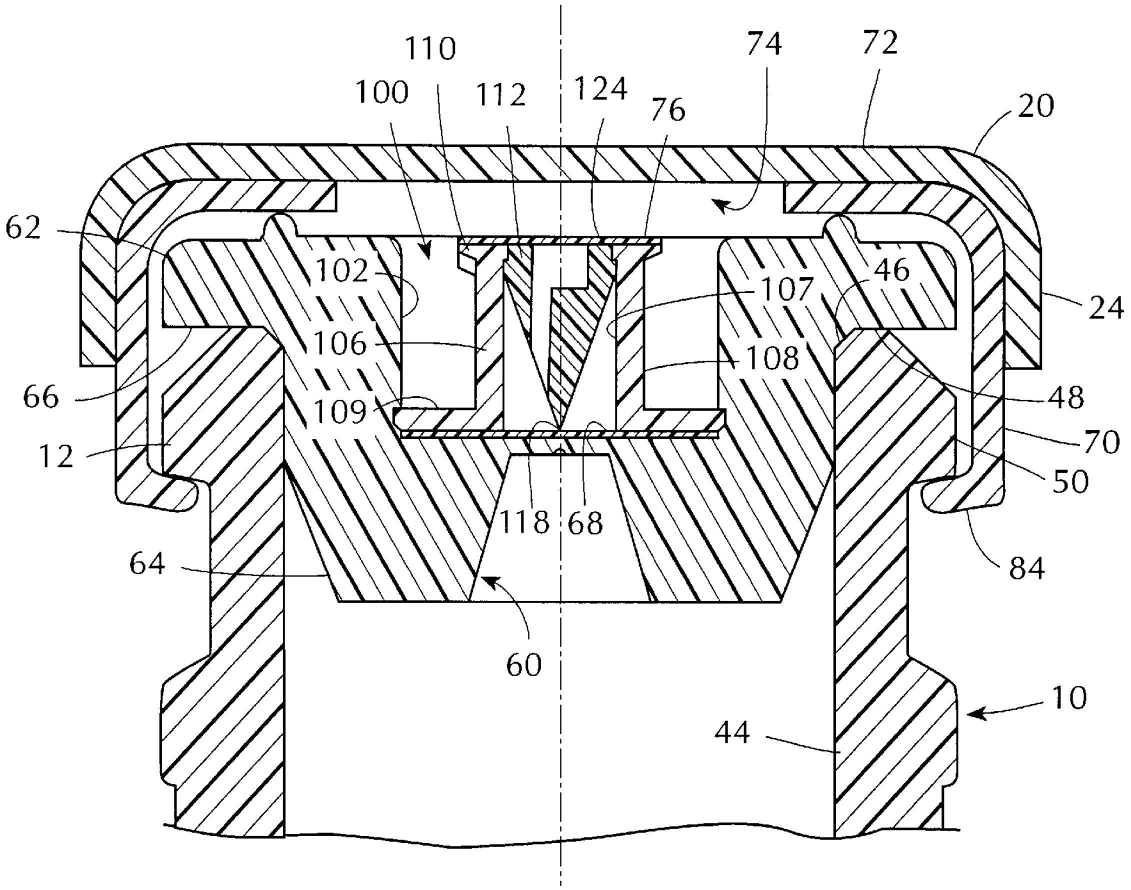
FIG. 6 is a sectional view of the neck portion of the container, the stopper with the spike access means and the cap taken along the line 5—5 of FIG. 1A.
Figure 8:
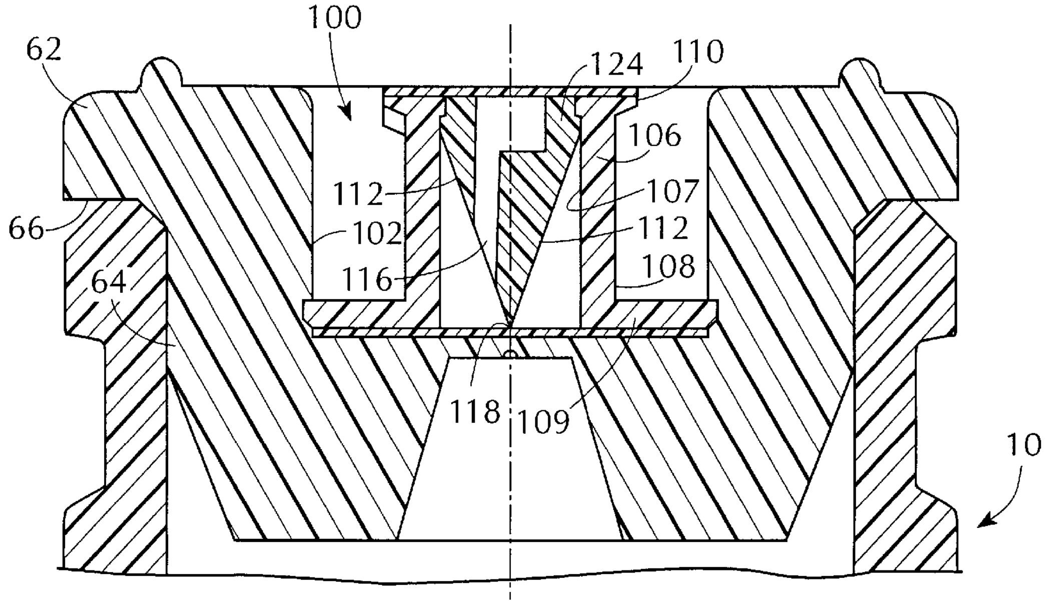
FIG. 8 is an enlarged sectional view of the male spike housing and spike shown in FIG. 6.

Referring to FIGS. 5, 6 and 8, the container 10 comprises a neck portion 12 having an interior surface 44, and interior radial end surface 46 on the top end portion of the interior surface 44, and transverse end surface 48. The interior radial surface and the transverse end surface form the mouth of container 10. The neck portion 12 further comprises an exterior surface which, adjacent to the transverse end surface 48, evolves into an exterior radial ring 50. The exterior radial ring is adapted to facilitate the holding of the closure assembly, described later.

The mouth of the container is to receive an elastomeric stopper 60, as shown in FIG. 6. The elastomeric stopper 60 comprises a head 62 and integral therewith a skirt 64. The head 62 comprises: a flange 66 extending laterally outwardly from skirt 64 and is adapted to cover transverse end surface 48 of container 10; stopper membrane 68; and sterility seal 69 which are designed to be pierced by the spike.

As best seen in FIG. 6 the container 10, after being filled with the desired amount of medical fluid, is sealed with the elastomeric stopper 60. To hold the elastomeric stopper securely in place, a cylindrical collar 70 is fastened over a portion of the elastomeric stopper 60 and the neck portion 12 of the container 10. The cylindrical collar 70 comprises:

a flat top portion 72 having a central opening therein 74 which opening is optionally covered by an upper sterility seal 76; and an inwardly projecting ring 84 which securely holds stopper 60 in container 10.

Referring to FIGS. 6 and 8, spike housing generally designated as 100 is located in the upper center portion of stopper 60 and integral therewith, comprises:

cylindrical wall 102; and stopper membrane 68 which forms the bottom, horizontal wall of the spike housing. Spaced from stopper membrane 68 and parallel therewith is optional lower sterility seal 69 which faces the content of container 10.

Within the spike housing there is located a luer connector which comprises:

a vertical cylindrical element 106 constituting the male portion in the spike housing having an outside surface 108, and an inside surface 107 facing spike 112;

locking ears 110 on top portion of said vertical cylindrical element to securely hold a female element; and spike 112.

The vertical cylindrical element 106 terminates in a horizontally oriented bottom portion 109 which extends into cylindrical wall 102 of spike housing 100 to firmly hold the luer connector in the elastomeric stopper 60.

The spike comprises:

a cylindrical shaft having a channel 116 therein, terminating in a sharp tip 118 at the lower end thereof; and a slideable plunger element 124 on the top portion thereof tightly facing inside surface 107 of cylindrical male element to provide for a leak-proof seal when spike 112 is forced towards the content of the container.

Figure 9:
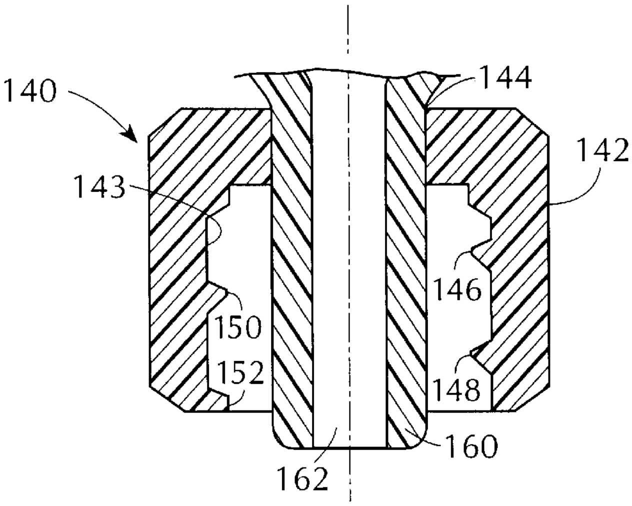
FIG. 9 is a female connector which is to engage the male spike housing shown in FIG. 8.
Figure 10:
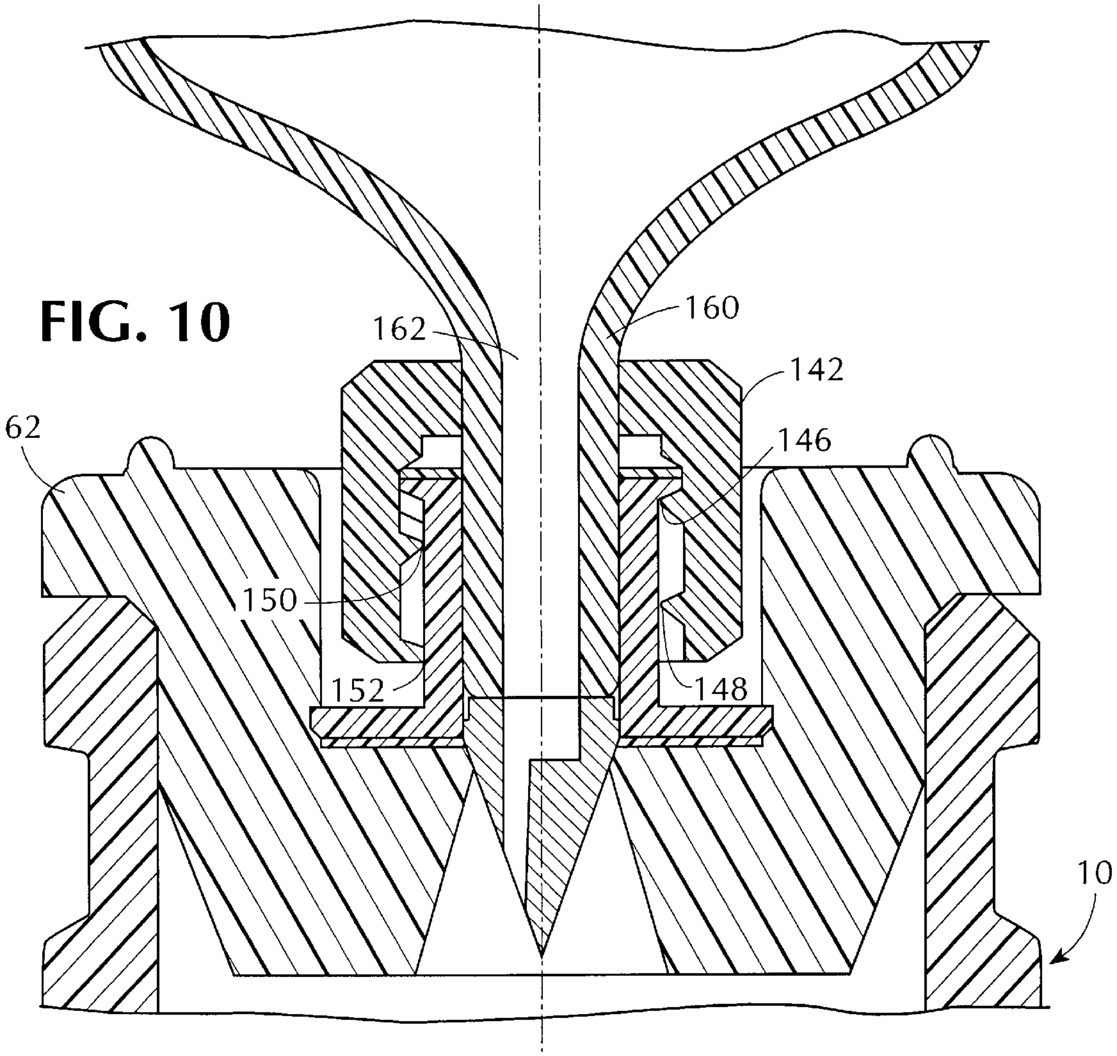
FIG. 10 shows the female connector shown in FIG. 9 engaging male spike housing shown in FIG. 9.

The female luer connector is shown in FIG. 9 prior to its engagement with the male luer connector and in FIG. 10, when it engages the male element of the luer connector.

The female luer connector 140 shown in FIG. 9 comprises: cylindrical outside wall 142 and cylindrical inside wall 143 having an opening in their center portion for accommodating a tubing within the inside wall. Cylindrical ring 144 located in the top center portion of cylindrical inside wall 143 tightly holds tubing 160 which has a fluid communicating channel 162. Cylindrical inside wall 143 further comprises integral screw threads 146, 148, 150 and 152 which, upon connecting the female luer connector to the male luer connector, engages locking ears 110 on the male luer connector.

When it is desired to deliver medical fluid from container 10 to a patient, the cylindrical cap 18 is removed exposing the upper sterility seal 76 (optionally present), which is also removed manually. Upon removal of the upper sterility seal male luer connector 106 is exposed to which female luer connector 140 is attached by twisting the female luer connector. The female luer connector engages by its threads 146, 148, 150 and 152 the locking ears 110 on the male luer connector.

Upon turning the female luer connector 140, spike 112 is being forced to move toward the content of the container 10, first penetrating stopper membrane 68, followed by penetration of lower sterility 69 (optionally present) to establish fluid communication with the content of the container 10. As spike 112 travels downward into the container, slidable plunger 124 on spike 112 provides leak-proof contact between it and internal cylindrical wall of luer connector 107. The medical fluid in the container is ready for delivery to the patients by turning the container upside-down.

Materials of Construction and Use

The elastomeric stopper used in conjunction with the spike access means of the present invention is fluid impervious, resilient, and inert without leachable additives therein in order to prevent any alteration of the product contained in the container. It may be of a single component or a blend of components. Examples of materials include synthetic and natural rubbers, such as butyl rubber, isoprene rubber, silicone rubber, halogenated rubber, ethylene propylene therpolymer and the like. Specific examples of a synthetic elastomeric rubber include the $CH_2CF_2$—$C_3F_6$ ($C_3F_5H$) and the $C_2F_4$—$C_2F_3OCF_3$ series of elastomers made by Dupont under the trade names of VITON® and CARLEZ®; the fluoro-silicone rubbers, such as those made by Dow Corning under the trade name of SILASTIC®; and polyisobutylenes, such as VISTANEX MML-100 and MML-140; and halogenated butyl rubber, such as CHLOROBUTYL 1066, made by Exxon Chemical Company.

These or other suitable elastomers may be made into the desired stopper configuration by known methods. Such methods conventionally include the use of a curing agent, a stabilizer and a filler and comprise a primary and a secondary curing step at elevated temperatures.

The container used in conjunction with the present invention may be of glass or a polymeric material, i.e., plastic, which are well known in the pharmaceutical industry. When the container is made of glass, it is in the shape of a vial or bottle. Polymeric materials are preferred for reasons of economy and safety. The plastic containers may be in the shape of a vial, bottle or bag. The vial or bottle is of rigid or semi-flexible polymeric material, while the bag is of a pliable polymeric material. In all shapes the container is provided with a neck portion which is rigid and retains its configuration so that it is capable of being hermetically sealed by elastomeric stopper/spike access means of the present invention. The container may have a volume capacity of from 5 ml to 1000 ml or more, preferably about 10 ml to 500 ml.

The container may be of various configuration such as cylindrical, rectangular and oval and may be in the form of a bag, bottle or vial and may be constructed with rigid, semi-rigid or pliable walls. The mouth of the container, however, should be of cylindrical configuration and constructed form rigid or at least semi-rigid material.

The mouth of the container is to receive the elastomeric stopper. The external diameter of the stopper is slightly larger than the internal diameter of the neck of the container so that on insertion of the stopper into the mouth of the container, a tight, hermetic seal is achieved.

The cylindrical collar is preferably made of metal, such as aluminum, while the spike housing and spike are of hard plastic known by the prior art and used in conjunction with pharmaceutical fluids.

Prior to use, the container and component parts of the closure are sterilized and the container is filled with a pharmaceutical fluid, such as a parenteral solution. The stopper containing the spike housing and spike with the luer connector thereon is inserted hermetically sealing the content of the container. Cylindrical collar is then crimped onto the container to securely hold the stopper in the container. Lastly, the cap is snapped onto the cylindrical collar to complete the closing of the container.

Upon requirement to withdraw the pharmaceutical fluid, the cap is removed by unsnapping it from the cylindrical collar and removing the upper sterility seal from the spike housing thereby exposing the male luer connector on the spike housing and male luer element on the spike. A female luer connector having an IV line attached thereto or being integral therewith is then made to engage the male luer connector and male luer element. The female luer connector is slowly screwed further into the male connectors thereby forcing the spike towards the stopper membrane and sterility seal which the sharp tip of the spike ruptures. Upon rupture, fluid communication is established between the content of the container and IV line attached to the female luer connector. To deliver the pharmaceutical fluid to the desired site, the container is turned upside down thereby allowing the pharmaceutical fluid to travel from the container to the site by gravity.

PARTS LIST

| | |
|---|---|
| Container | 10 |
| Neck portion of container | 12 |
| Side portion of container | 14 |
| Bottom portion of container | 16 |
| Cylindrical cap (of closure assembly) | 18 |
| Flat top portion of cap | 20 |
| Bottom rim portion of cap | 22 |
| Cylindrical side portion of cap | 24 |
| Interior surface of the neck portion of container | 44 |
| Interior radial end surface of the neck portion of container | 46 |
| Transverse end surface of container | 48 |
| Exterior radial ring of neck portion of container | 50 |
| Elastomeric stopper | 60 |
| Head of elastomeric stopper | 62 |
| Skirt of elastomeric stopper | 64 |
| Flange of head of elastomeric stopper | 66 |
| Stopper membrane | 68 |
| Lower sterility seal (TYVEC sterility seal) | 69 |
| Cylindrical collar | 70 |
| Flat top portion of cylindrical collar | 72 |
| Central opening in the flat top portion of the cylindrical collar | 74 |
| Upper sterility seal (TYVEC sterility seal) | 76 |
| Cylindrical side portion of cylindrical collar | 78 |
| Inwardly projecting ring | 84 |
| Spike housing | 100 |
| Cylindrical wall of spike housing | 102 |
| Male portion of luer connector | 106 |
| Inside surface of cylindrical male element | 107 |
| Outside cylindrical wall surface on male element | 108 |
| Bottom portion of male element | 109 |
| Locking ears | 110 |
| Spike | 112 |
| Channel within spike | 116 |
| Sharp tip of spike | 118 |
| Slidable plunger on spike | 124 |
| Female luer connector | 140 |
| Cylindrical outside wall of female luer connector | 142 |
| Cylindrical ring of female luer connector | 144 |
| Screw threads on inside all of female luer connector | 146, 148, 150, 152 |
| Tubing | 160 |
| Channel in tubing | 162 |

The present invention has been described in connection with the preferred embodiment shown in the drawings, however, various changes and modifications will be apparent to those skilled in the art.

What is claimed is:

1. A closure assembly/container combination, wherein said container contains a medical fluid therein, and said closure assembly having a needleless access means allowing withdrawal of said medical fluid from the container by the use of an intravenous tubing attached to said needlesless access means, said closure/container combination comprising:

a container (a);

a closure (b); and a cap (c), wherein said container (c) containing a medical fluid therein, having a neck portion terminating in an open end;

wherein said closure assembly (b) inserted into the open end of said container, comprising:

(1) an elastomeric stopper for hermetically sealing the container at its open end;

(2) a cylindrical collar fastened over portions of the elastomeric stopper and the container, said cylindrical collar having a central opening in its flat top portion to allow access to a spike access means located in the elastomeric stopper;

(3) a spike access means, located in the upper center portion of said elastomeric stopper, comprising:

(I) a spike housing defined by a cylindrical side wall, a horizontal stopper membrane forming the bottom of the spike housing, and a removable sterility seal on the horizontal top portion of the spike housing;

(ii) a spike, located in said spike housing, comprising: a top portion, a side portion, and a bottom portion; said top portion having a male element on the upper end thereof, a cylindrical shaft extending through the male element thereon, a cylindrical shaft extending through the male element having a fluid communicating channel therein and terminating in a sharp tip at the other, bottom end thereof for piercing the membrane area in said elastomeric stopper;

(iii) A male connector on the exterior of the spike housing; said male element on the upper end of the spike and said male connector on the exterior of the spike housing being designed to twistably engage a female coupling to force and move the spike towards and penetrate the horizontal stopper membrane and thereby establish fluid communication with the medical fluid contained in said container; and wherein said cap (c) is covering the cylindrical collar over the container.

2. The closure assembly/container combination of claim 1 wherein said container is made of glass.

3. The closure assembly/container combination of claim 2 wherein said container is a vial.

4. The closure assembly/container combination of claim 2 wherein said container is a bottle.

5. The closure assembly/container combination of claim 1 wherein said container is a made of a polymeric material.

6. The closure assembly/container combination of claim 5 wherein said container is a pouch or a bag.

7. The closure assembly/container combination of claim 1 wherein said medical fluid is a parenteral liquid.

8. The closure assembly/container combination of claim 7 wherein said parenteral liquid is an x-ray contrast medium.

9. The closure assembly/container combination of claim 7 wherein said parenteral liquid is a therapeutic liquid.

10. The closure assembly/container combination of claim 1 wherein the volume capacity of said container is of from about 5 ml to about 1000 ml.

11. A closure assembly/container combination, said container having a medical fluid therein, said closure assembly having a needleless access means allowing withdrawal of said medical fluid from said container by the use of an intravenous tubing attached to said needleless access means, said closure/container combination comprising:

a container (a);

a closure assembly (b); and a cap (c) wherein said (a) container having a medical fluid therein, comprises:

a neck portion having an interior radial surface and a transverse end surface forming the mouth of said container, an exterior surface which, with said transverse end surface, forms a radial ring to receive and hold a cylindrical collar, (b) a closure assembly inserted into the mouth of said container comprising:

an elastomeric stopper (1), a cylindrical collar (2) and a spike access means (3), wherein said (1) elastomeric stopper comprises:

a head portion and a skirt portion, said head portion having: a flange extending laterally outwardly form said skirt portion and is designed to cover the mouth of the container; and a recessed open central area designed to receive said spike access means; and said skirt portion projecting into the container sealing the medical fluid contained therein;

(2) cylindrical collar comprising:

a flat top portion having a central opening therein superimposed on the recessed open area in the head portion of the elastomeric stopper;

a cylindrical side portion having an inner wall, an outer wall, and a bottom portion;

said inner wall having an inwardly projecting ring positioned below the exterior radial ring on the container to securely hold the elastomeric stopper in the container;

(3) spike access means located in the upper center portion of said elastomeric stopper, comprises:

(i) a spike housing defined by a cylindrical side wall, a horizontal stopper membrane forming the bottom of the spike housing, a horizontal sterility seal covering the stopper membrane on the underside of the stopper membrane forming a barrier between the stopper membrane and the medical fluid in the container and a removable sterility seal on the horizontal top portion of the spike housing;

(ii) a spike, located in said spike housing, comprises: a top portion, a side portion, and a bottom portion;

said top portion having a male element thereon, a cylindrical shaft extending through the male element having a fluid communicating channel therein and terminating in a sharp tip at the other, bottom end thereof for piercing the membrane area in said elastomeric stopper;

said side portion on the upper part thereof having a slidable plunger pressing against internal cylindrical wall of a male connector;

(iii) a male connector on the exterior of the spike housing;

said male element on the upper end of the spike and said male connector on the exterior of the spike housing being designed to twistably engage a female coupling to force and move the spike towards and penetrate the horizontal stopper membrane and the sterility seal and thereby establish fluid communication with the medical fluid contained in said container; and (c) cap enclosing the elastomeric stopper, the cylindrical collar and spike access means to maintain the closure assembly free form contamination.

12. The closure assembly/container combination of claim 11 wherein said container is made of glass.

13. The closure assembly/container combination of claim 12 wherein said container is a vial.

14. The closure assembly/container combination of claim 11 wherein said container is a bottle.

15. The closure assembly/container combination of claim 11 wherein said container is made of a polymeric material.

16. The closure assembly/container combination of claim 15 wherein said container is made of a flexible or pliable polymeric matieral.

17. The closure assembly/container combination of claim 11 wherein said container is a pouch or bag.

18. The closure assembly/container combination of claim 11 wherein said medical fluid contained in said container is an x-ray contrast medium.

19. The closure assembly/container combination of claim 11 wherein said medical fluid contained in said container is a parenteral liquid.

20. The closure assembly/container combination of claim 11 wherein the volume capacity of said container is of from about 10 ml to about 500 ml.

* * * * *